(12) United States Patent
Kreckel et al.

(10) Patent No.: US 7,355,700 B2
(45) Date of Patent: Apr. 8, 2008

(54) AUTOMATED INSPECTION SYSTEM AND METHOD

(75) Inventors: Achim Kreckel, Mainz (DE); Christian Laue, Mainz (DE); Edgar Maehringer-Kunz, Muenster-Sarmsheim (DE)

(73) Assignee: International Business Machines Corporation, Armonk, NY (US)

( * ) Notice: Subject to any disclaimer, the term of this patent is extended or adjusted under 35 U.S.C. 154(b) by 148 days.

(21) Appl. No.: 11/266,742

(22) Filed: Nov. 3, 2005

(65) Prior Publication Data

US 2006/0126061 A1 Jun. 15, 2006

(30) Foreign Application Priority Data

Dec. 10, 2004 (EP) .................................. 04106458

(51) Int. Cl.
*G01J 3/00* (2006.01)
(52) U.S. Cl. .................................... 356/300; 356/237.6
(58) Field of Classification Search ................ 356/300, 356/240.1, 237.6; 250/559.14, 223 B, 559.45; 382/152, 141, 142
See application file for complete search history.

(56) References Cited

U.S. PATENT DOCUMENTS

| | | | | |
|---|---|---|---|---|
| 6,157,038 A | * | 12/2000 | Swain et al. | ............. 250/459.1 |
| 6,606,403 B2 | | 8/2003 | Freifeld | |
| 7,282,710 B1 | * | 10/2007 | Black et al. | ................ 250/306 |
| 2004/0125371 A1 | * | 7/2004 | Chang et al. | ............... 356/318 |

* cited by examiner

*Primary Examiner*—Gregory J. Toatley, Jr.
*Assistant Examiner*—Tri Ton
(74) *Attorney, Agent, or Firm*—Roy W. Truelson

(57) ABSTRACT

An automated system for illuminating and inspecting the inner surface areas of tubular samples, especially stents, is disclosed. The system comprises rotatable means for receiving the sample to be inspected; at least one fluorescent surface area arranged in the immediate vicinity of the sample to be inspected; an UV-light source for illuminating the at least one fluorescent surface area; an electronic line-scan camera for inspecting the sample; and a computer based electronic imaging system, functionally connected to the camera, whereby the imaging system creates a line-by-line image of an area extending along the length of the sample as it rotates under the camera.

5 Claims, 3 Drawing Sheets

AUTOMATED INSPECTION SYSTEM AND METHOD

FIELD OF THE INVENTION

This invention relates generally to inspection systems, and more specifically to an automated system for illuminating and inspecting objects, such as cardiovascular stents and other precision cut tubes and components.

BACKGROUND OF THE INVENTION

Stents are small, intricately cut tubes, generally made of materials such as stainless steel. Cardiovascular stents are permanently placed in a blood vessel to act as scaffolding to keep an occluded artery open. In use, cardiovascular stents are inserted into the artery on a catheter and are typically deployed by expanding a very small balloon at the end of the catheter upon which the stent is mounted.

Cardiovascular stents must meet stringent requirements to work properly. If the stent contains any rough or sharp edges, it will damage blood cells or the blood vessel in which it is inserted. This can lead to further atherosclerotic plaquing, emboli or thrombi, and result in potentially life threatening situations.

This invention relates to an illumination and inspection system for stents and other similar parts that take the form of a small precisely machined tube.

Lasers are typically used to cut stents. This process, while highly precise, can occasionally produce defective parts. Stents tend to be fairly small, with diameters approximating 1 mm. After processing, the individual cut features on a stent range from 50 to 200 microns in size. Accordingly, small changes in manufacturing process parameters such as laser power, tubing diameter, or mechanical jitter can cause defects. Such defects may include an out of tolerance feature size or a malformed feature.

Since stents are used in the heart and other critical areas of blood flow, a failure in the function of the stent could be life threatening. Thus, manufacturers of stents typically employ 100% inspection procedures. A human operator utilizing a 50× optical power stereo-microscope typically inspects for visual defects. Dimensional inspection is typically done by a human operator utilizing a Profile Projector. Alternatively, this inspection can be done automatically by utilizing a vision system.

The problems associated with either the manual or automatic approaches to inspection are numerous. First, human error makes visual inspection of products less than completely effective. Also, such manual inspection is relatively slow and thus a relatively costly aspect of the manufacturing process. Furthermore, the pass/fail criteria of the profile projector using overlays, as is typically employed in manual inspection, does not generally provide any numeric dimensional data that would otherwise be useful for process control. In addition, when inspecting the outer and the inner surface of a stent, both surfaces are typically illuminated at the same time, leading to reflexes that will prevent an automatic inspection.

U.S. Pat. No. 6,606,403 B2 discloses an automatic system for illuminating, inspecting and measuring stents and other precision cut tubes and components made of a linear array electronic camera with a lens, a light source to provide necessary illumination to create an image on the linear array camera, a mandrel onto which the tube is mounted during inspection, a rotary stage for rotating the mandrel, and a computer based electronic imaging system that creates a line-by-line image of the stent as it rotates under the camera. However, the system is only able to inspect the outer surface of the stent.

SUMMARY OF THE INVENTION

It is therefore an object of the present invention to provide an automated inspection system capable of selectively illuminating either only the outer or only the inner surface of the sample to be inspected at a time.

It is a further object of the present invention to provide a method to automatically inspect the outer or inner surface of a sample.

These and other objects and advantages are achieved by the system disclosed in claim 1 and the method disclosed in claim 10.

Advantageous embodiments of the invention are disclosed in the dependent claims.

DETAILED DESCRIPTION OF THE PREFERRED EMBODIMENT

As previously described, cardiovascular stents are permanently placed in a blood vessel to act as scaffolding to keep an occluded artery open. In use, cardiovascular stents are inserted into the artery on a catheter and are typically deployed by expanding a very small balloon at the end of the catheter upon which the stent is mounted.

When producing such stents, these have to be inspected with respect to different defects. During this inspection, the outer surface area as well as the inner surface area must be inspected. However, the basic problem is to find an illumination method that allows selective illumination of either the outer surface area or the inner surface area within a confined space. As soon as both sides are illuminated simultaneously, stray reflections will occur, which prevent an exact automatic inspection.

Today, when inspecting tubular samples (e.g., cardiovascular stents), the samples are placed on two feeder rollers, which can be rotated. Thus, the stents can be placed in any position and can be inspected from all sides. The inspection is carried out using an illumination from the outside, i.e., the outer and the inner surface area are illuminated simultaneously.

Subsequently, the outer and inner surface area of the stent is brought into focus successively, and the stent is inspected. Due to the simultaneous illumination of both sides, images having very intensive stray reflections will occur. This, however, will hamper a reproducible manual inspection and, at the same time, prevents an automatic inspection using image processing algorithms.

The present invention uses fluorescent light as a light source for extensive diffuse illumination in the immediate vicinity of the sample to be inspected.

Figure 1:
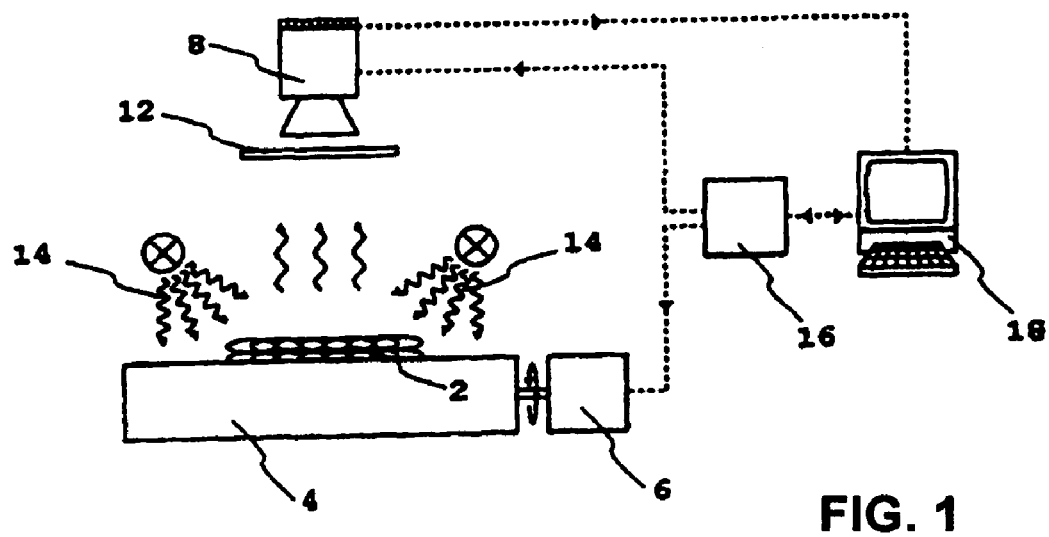
FIG. 1 schematically depicts a front view of a first setup of the illuminating and inspection system according to the invention.

FIG. 1 schematically depicts a front view of the setup of the illumination and inspection system according to the invention. The tubular sample 2 to be inspected (e.g., a cardiovascular stent), is put on a rotatable means (e.g., two cylinders or feeder rollers) 4. These cylinders or feeder rollers can be rotated by a step motor 6 and either have a fluorescent surface or are completely made from a fluorescent material. When illuminated with blue light (UV light) 14, the cylinders emit fluorescent green/yellow light which, in turn, illuminates the stent 2. The stent 2 is then inspected from above by means of a line-camera 8. A long-pass filter 12 in front of the camera 8 filters out the blue light reflected from the stent surface and only the fluorescent light passes through.

Figure 2:
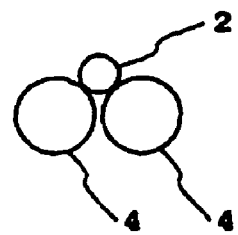
FIG. 2 schematically depicts a side view of the setup of the illuminating and inspection system according to FIG. 1.

As can be seen from FIG. 2, which schematically depicts a side view of the setup of the illumination and inspection system according to FIG. 1, the sample 2 to be inspected is arranged on said rotatable means such that the top edge of the sample 2 lies above the top edge of the cylinders 4. Due to this geometrical setup of the stent 2 and the cylinders 4, the fluorescent light only illuminates the inner surface area of the stent. The outer surface area is in the dark and does not reflect any light into the direction of the camera.

A controller 16 is connected to a PC 18 and triggers the line-camera 8 and the step motor 6. The line-camera 8 takes pictures of the stent surface while the stent 2 is rotated by the cylinders 4. Line-pictures are taken for various angular stent positions and are sent to the PC 18. Afterwards the line-pictures are combined to get a full 360° view of the stent's inner surface area. This 360°-picture is inspected on the PC 18 by image processing algorithms.

According to the invention, an indirect illumination of the sample to be inspected is used. By illuminating the cylinders with UV light, the cylinders start to glow. Thus, extensive diffuse glowing light sources on both sides of the sample to be inspected are achieved. The UV light source may consist of UV-LEDs, which emit light at 405 nm.

It is, however, possible to use transparent cylinders having a backlight illumination instead of using fluorescent cylinders.

Figure 3:
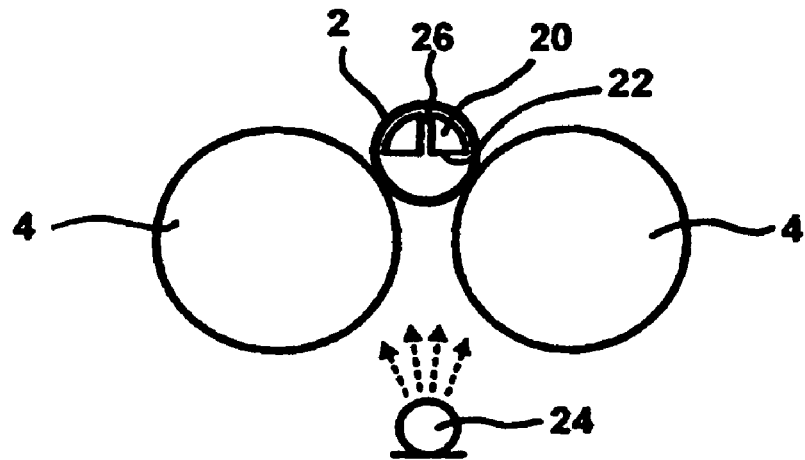
FIG. 3 schematically depicts a side view of a second setup of the illuminating and inspection system according to the invention.

FIG. 3 schematically depicts a side view of a second setup of the illuminating and inspection system according to the invention. As can be taken from the figure, a cylinder 20 is inserted into the sample 2 to be inspected, e.g., the stent. The cylinder 20 is flattened on its lower side, i.e., the side which points in the direction of the cylinders or feeder rollers 4. The flattened side carries a fluorescent layer 22. When illuminating the fluorescent layer 22 with UV light 24 from below, this layer starts to glow. Observation of the inner surface area of the stent is done from above through a slit 26 in the cylinder 20 inserted into the stent 2. No visible light reaches the outer surface area of the stent which is visible from above. Thus, by indirectly illuminating the inner surface area of the stent, using fluorescent light, no stray reflections will occur and the inner surface area can be easily automatically inspected.

Figure 4A:
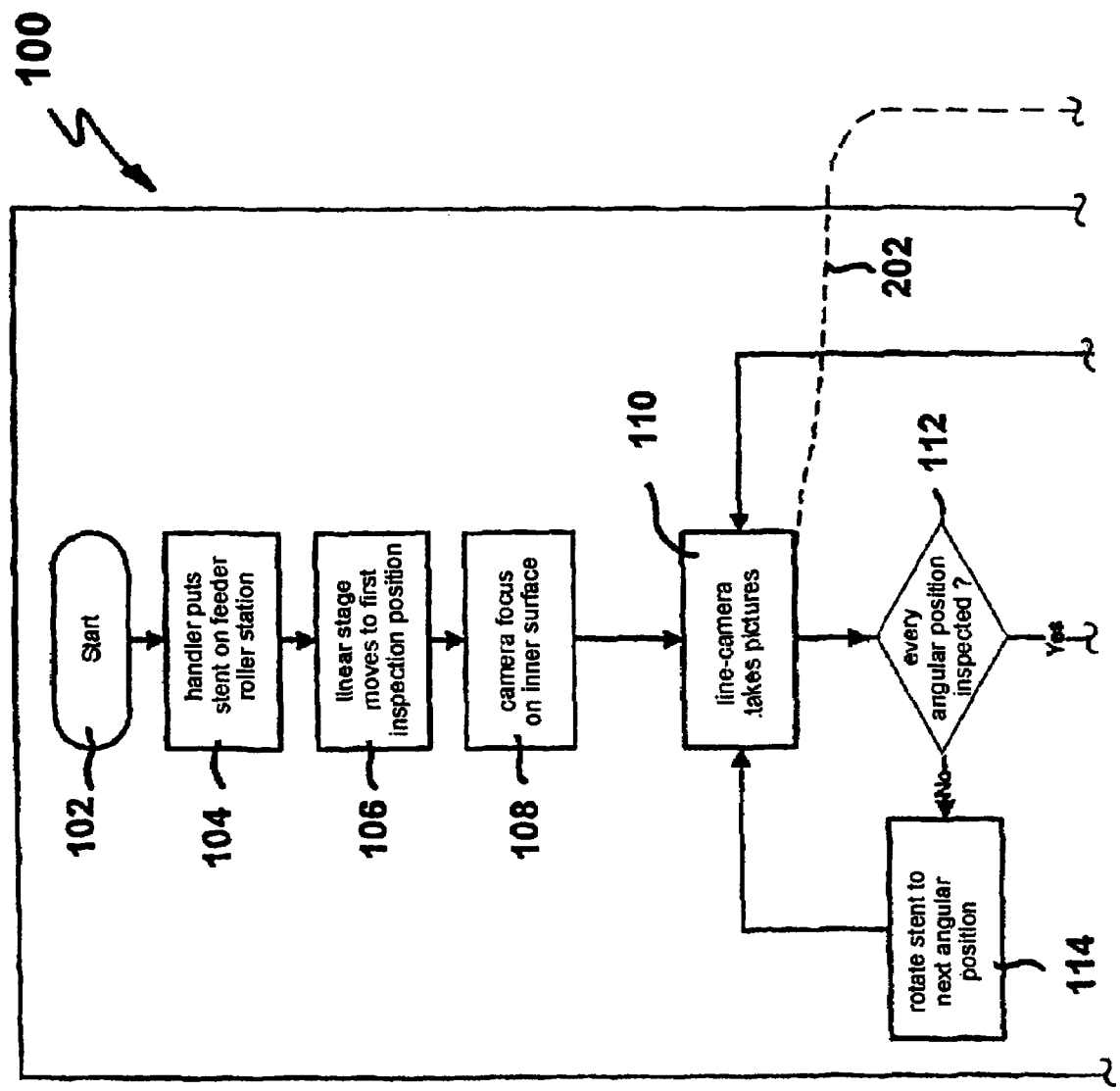
FIG. 4 is a flow chart illustrating the steps of the method according to the invention.
Figure 4B:
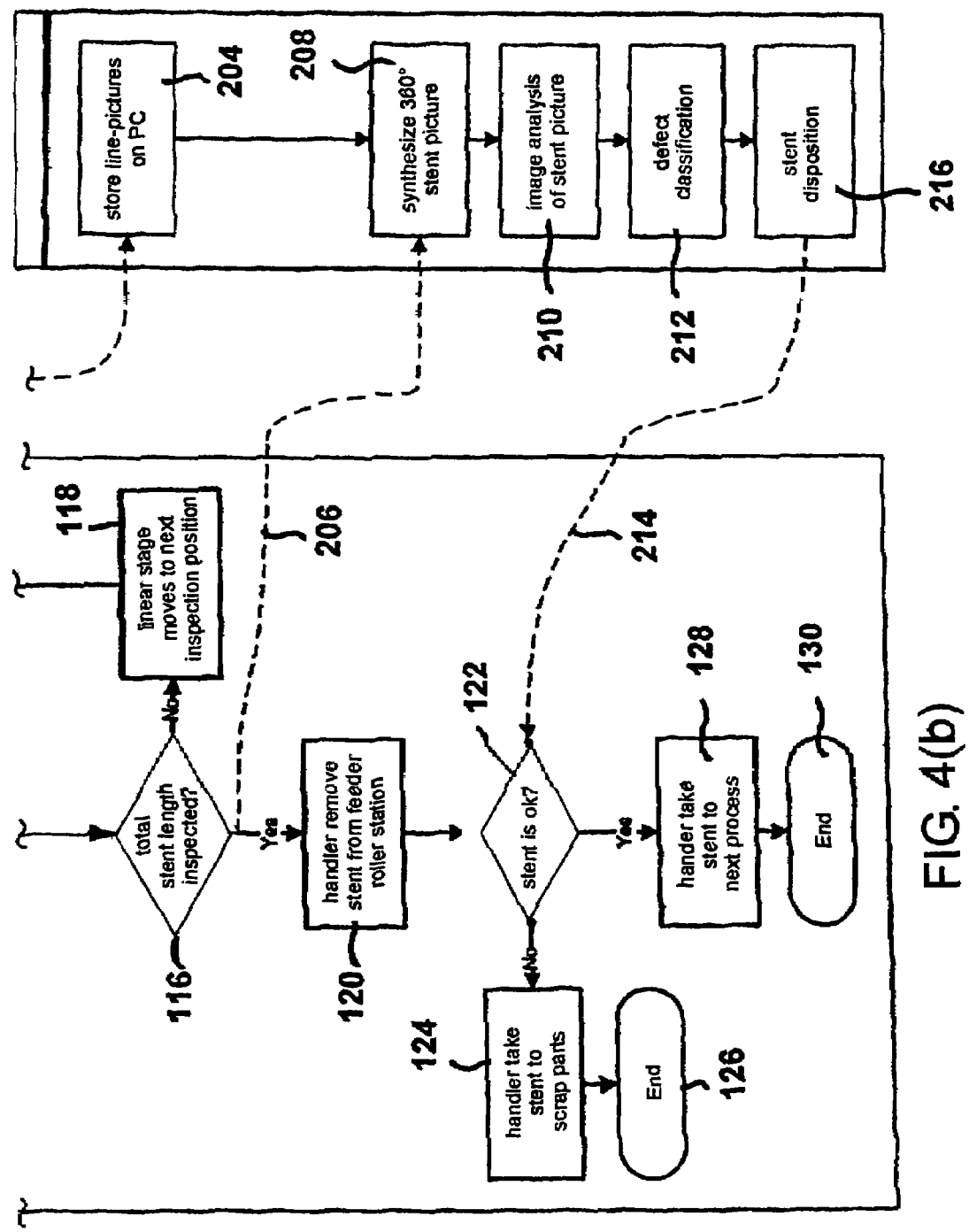

FIG. 4 is a flow chart illustrating the steps of the method 100 according to the invention.

When starting the process at Step 102, a first handler puts the stent to be inspected on the rotatable means, i.e., the cylinders or feeder rollers (Step 104). Next, a linear stage moves to a first inspection position (Step 106), where the camera focuses on the inner surface of the stent (Step 108). Now the line-camera takes respective pictures of the inner surface area of the stent (Step 110). Next, it is checked (Step 112) whether every angular position of the stent has been inspected. If this is not the case, the process passes on to Step 114, where the stent is rotated to the next angular position to be inspected. In case all angular positions have been inspected, the system moves on to Step 116 where it is checked whether the total length of the stent has been inspected. If this is not the case, the process passes on to Step 118, where the linear stage moves the stent to the next inspection position. In case the total length of the stent has been inspected, the system on to Step 120, where the stent is removed from the rotatable means by a handler. Subsequently, it is decided whether the stent is ok or not ok (Step 122). If this is not the case, a handler will take the respective stent to scrap parts (Step 124) and the process ends (Step 126). In case the stent is ok (Step 128), a handler takes it to the next processing step (Step 130) and the process ends (Step 132).

At the time, the line-camera starts to take pictures of the stent (Step 110), these pictures are transferred (dashed line 202) to a PC forming part of an image processing system 200, and processing of the respective data is started. Every picture the camera takes is transferred to the PC and stored (Step 204). When the total length of the stent has been inspected (Step 116) and all pictures have been transferred to the PC (dashed line 206), a 360° stent picture is synthesized (Step 208) by the image processing system 200. The picture is then analyzed (Step 210) and eventually found defects are classified (Step 212). For further disposition (Step 216; dashed line 214) of the inspected stent, the data is sent to Step 122, where it is decided whether the stent should be taken to scrap parts or whether it can be taken to the next processing step.

It is clear from the above description, that not only cardiovascular stents may be inspected by the system and method according to the invention. Rather, all tubular samples that are built so that light can pass through their surfaces, can be inspected.

What is claimed is:

1. A method of inspecting an inner surface area of a tubular sample, comprising the steps of:
   positioning said tubular sample with respect to a pair of cylindrical illuminating members, each said cylindrical illuminating member having a respective longitudinal axis, wherein said longitudinal axes of said cylindrical illuminating members are parallel, said tubular sample being positioned outside said cylindrical illuminating members and in a longitudinal axis parallel to the longitudinal axes of said cylindrical illuminating members;
   wherein said tubular sample is positioned with respect to an inspection location with a longitudinal edge of an outer surface area of said tubular sample nearest said inspection location being closer to said inspection location than any longitudinal edge of said cylindrical illuminating members, and with at least one longitudinal edge of said inner surface area of said tubular sample being farther from said inspection location than the respective longitudinal edges of said cylindrical illuminating members which are closest to said inspection location; and
   inspecting said tubular sample from said inspection location while said tubular sample is illuminated by light emitted from the surfaces of said cylindrical illuminating members.

2. The method according to claim 1, wherein said tubular sample comprises a cardiovascular stent.

3. The method according to claim 1, wherein said tubular sample rests on said cylindrical illuminating members.

4. The method according to claim 3, further comprising the step of:
   rotating said cylindrical illuminating members to cause rotation of said tubular sample during said inspecting step.

5. The method according to claim 1, wherein said cylindrical illuminating members comprise respective fluorescent surfaces for illuminating said inner surface area of said tubular sample, said fluorescent surfaces being stimulated by an external source to emit light for illuminating said inner surface area of said tubular sample.

* * * * *